(12) United States Patent
Jones et al.

(10) Patent No.: US 7,795,038 B2
(45) Date of Patent: *Sep. 14, 2010

(54) HIGH-DENSITY LIPOPROTEIN ASSAY DEVICE AND METHOD

(75) Inventors: Ronald M. Jones, Mountain View, CA (US); Thomas E. Worthy, Walnut Creek, CA (US); Jeffrey Shindelman, Castro Valley, CA (US); Neal F. Bellet, Walnut Creek, CA (US); Anthony J. Nugent, Dublin, CA (US)

(73) Assignee: Cholestech Corporation, Hayward, CA (US)

(*) Notice: Subject to any disclaimer, the term of this patent is extended or adjusted under 35 U.S.C. 154(b) by 462 days.

This patent is subject to a terminal disclaimer.

(21) Appl. No.: 10/410,671

(22) Filed: Apr. 8, 2003

(65) Prior Publication Data

US 2003/0224471 A1 Dec. 4, 2003

Related U.S. Application Data

(60) Provisional application No. 60/371,093, filed on Apr. 9, 2002.

(51) Int. Cl.
 *G01N 33/53* (2006.01)

(52) U.S. Cl. .............................. 436/518; 435/4; 435/7.1; 435/11; 435/287.1; 435/287.7; 435/287.9; 435/288.7; 436/71; 436/169; 436/170; 436/175; 436/177; 436/178; 422/50; 422/56; 422/58; 422/68.1; 422/101; 422/104

(58) Field of Classification Search ................ 435/4, 435/7.1, 11, 287.1, 287.9, 288.7; 436/71, 436/169, 170, 175, 177, 178; 422/50, 56, 422/58, 68.1, 101, 104

See application file for complete search history.

(56) References Cited

U.S. PATENT DOCUMENTS

| 3,508,879 | A | 4/1970 | Findl et al. |
| 3,607,093 | A | 9/1971 | Stone |
| 3,791,933 | A | 2/1974 | Moyer et al. |
| 3,797,494 | A | 3/1974 | Zaffaroni |
| 3,907,642 | A | 9/1975 | Richmond |
| 3,907,645 | A | 9/1975 | Richmond |
| 3,925,164 | A | 12/1975 | Beaucamp et al. |

(Continued)

FOREIGN PATENT DOCUMENTS

CA 1211707 A 9/1986

(Continued)

OTHER PUBLICATIONS

International Search Report from PCT application No. PCT/US03/10420 mailed on Sep. 17, 2003.

(Continued)

*Primary Examiner*—Bao-Thuy L Nguyen
(74) *Attorney, Agent, or Firm*—Wilson Sonsini Goodrich & Rosati

(57) ABSTRACT

An assay device and method for measuring the concentration of HDL-associated cholesterol in a blood-fluid sample are described. The assay design prevents interference by reagents used for such removal with the HDL quantification reaction or with other assays carried out on the same sample. If desired, removal of non-HDL lipoproteins and assay of HDL cholesterol can be carried out without interruption of the assay.

21 Claims, 3 Drawing Sheets

U.S. PATENT DOCUMENTS

| | | |
|---|---|---|
| 3,983,005 A | 9/1976 | Goodhue et al. |
| 4,038,485 A | 7/1977 | Johnston et al. |
| 4,042,329 A | 8/1977 | Hochstrasser |
| 4,069,017 A | 1/1978 | Wu et al. |
| 4,125,372 A | 11/1978 | Kawai et al. |
| 4,126,416 A | 11/1978 | Sears |
| 4,144,129 A | 3/1979 | Gruber et al. |
| 4,144,306 A | 3/1979 | Figueras |
| 4,152,390 A | 5/1979 | Nosco et al. |
| 4,153,668 A | 5/1979 | Hill et al. |
| 4,164,448 A | 8/1979 | Roeschlau et al. |
| 4,181,575 A | 1/1980 | Gruber et al. |
| 4,186,251 A | 1/1980 | Tarbutton |
| 4,188,188 A | 2/1980 | Willner et al. |
| 4,212,938 A | 7/1980 | Gruber et al. |
| 4,215,993 A | 8/1980 | Sanders |
| 4,216,245 A | 8/1980 | Johnson |
| 4,234,317 A | 11/1980 | Lucas et al. |
| 4,246,339 A | 1/1981 | Cole et al. |
| 4,248,829 A | 2/1981 | Kitajima et al. |
| 4,256,693 A | 3/1981 | Kondo et al. |
| 4,271,119 A | 6/1981 | Columbus |
| 4,313,734 A | 2/1982 | Leuvering |
| 4,366,244 A | 12/1982 | Pascal |
| 4,391,904 A | 7/1983 | Litman et al. |
| 4,399,362 A | 8/1983 | Cormier et al. |
| 4,435,504 A | 3/1984 | Zuk et al. |
| 4,477,575 A | 10/1984 | Vogel et al. |
| 4,503,144 A | 3/1985 | Deeg et al. |
| 4,533,629 A | 8/1985 | Litman et al. |
| 4,544,630 A | 10/1985 | Ziegenhorn et al. |
| 4,549,655 A | 10/1985 | Forsythe et al. |
| 4,552,839 A | 11/1985 | Gould et al. |
| 4,565,740 A * | 1/1986 | Golander et al. ............ 428/409 |
| 4,615,946 A | 10/1986 | Temple |
| 4,623,628 A | 11/1986 | Maaskant et al. |
| 4,632,901 A | 12/1986 | Valkirs et al. |
| 4,654,310 A | 3/1987 | Ly |
| 4,680,259 A | 7/1987 | Cumbo et al. |
| 4,743,560 A | 5/1988 | Campbell |
| 4,746,605 A | 5/1988 | Kerscher et al. |
| 4,756,828 A | 7/1988 | Litman et al. |
| 4,774,192 A | 9/1988 | Terminiello et al. |
| 4,814,077 A | 3/1989 | Furuyoshi et al. |
| 4,816,224 A | 3/1989 | Vogel et al. |
| 4,820,489 A | 4/1989 | Rothe et al. |
| 4,826,421 A | 5/1989 | Asano et al. |
| 4,826,721 A | 5/1989 | Obrecht et al. |
| 4,826,759 A | 5/1989 | Guire et al. |
| 4,826,761 A | 5/1989 | Arai et al. |
| 4,828,983 A | 5/1989 | Mcclune |
| 4,839,296 A | 6/1989 | Kennedy et al. |
| 4,839,297 A | 6/1989 | Freitag et al. |
| 4,849,340 A | 7/1989 | Oberhardt |
| 4,855,108 A | 8/1989 | Masuda et al. |
| 4,877,586 A | 10/1989 | Devaney, Jr. et al. |
| 4,877,746 A | 10/1989 | Jansson et al. |
| 4,910,134 A | 3/1990 | Yamanishi et al. |
| 4,920,046 A | 4/1990 | Mcfarland et al. |
| 4,943,522 A | 7/1990 | Eisinger et al. |
| 4,956,275 A | 9/1990 | Zuk et al. |
| 4,959,324 A | 9/1990 | Ramel et al. |
| 4,963,468 A | 10/1990 | Olson |
| 4,973,549 A | 11/1990 | Khanna et al. |
| 4,981,786 A | 1/1991 | Dafforn et al. |
| 4,987,085 A | 1/1991 | Allen et al. |
| 4,999,285 A | 3/1991 | Stiso |
| 4,999,287 A | 3/1991 | Allen et al. |
| 4,999,289 A | 3/1991 | Akiba |
| 5,075,078 A | 12/1991 | Osikowicz |
| 5,082,626 A | 1/1992 | Grage, Jr. |
| 5,087,556 A | 2/1992 | Ertinghausen |
| 5,110,724 A | 5/1992 | Hewett |
| 5,130,231 A * | 7/1992 | Kennedy et al. ............... 435/4 |
| 5,135,716 A | 8/1992 | Thakore |
| 5,135,873 A | 8/1992 | Patel et al. |
| 5,137,808 A | 8/1992 | Ullman et al. |
| 5,147,609 A | 9/1992 | Grenner |
| 5,149,505 A | 9/1992 | Englishe et al. |
| 5,156,954 A | 10/1992 | Mielke |
| 5,167,922 A | 12/1992 | Long |
| 5,171,688 A | 12/1992 | Hewett et al. |
| 5,204,063 A | 4/1993 | Allen |
| 5,213,964 A * | 5/1993 | Jones .......................... 435/11 |
| 5,213,965 A | 5/1993 | Jones |
| 5,215,886 A | 6/1993 | Patel et al. |
| 5,252,496 A | 10/1993 | Kang et al. |
| 5,260,221 A | 11/1993 | Ramel et al. |
| 5,260,222 A | 11/1993 | Patel et al. |
| 5,286,626 A | 2/1994 | Law et al. |
| 5,316,916 A | 5/1994 | Jones et al. |
| 5,320,968 A | 6/1994 | Seman et al. |
| 5,401,466 A | 3/1995 | Foltz et al. |
| 5,407,836 A | 4/1995 | Ziegenhorn et al. |
| 5,409,664 A * | 4/1995 | Allen .......................... 422/56 |
| 5,411,870 A | 5/1995 | Law et al. |
| 5,416,000 A | 5/1995 | Allen et al. |
| 5,417,863 A | 5/1995 | Varady et al. |
| 5,426,030 A * | 6/1995 | Rittersdorf et al. ............ 435/11 |
| 5,451,370 A | 9/1995 | Jones |
| 5,460,974 A | 10/1995 | Kozak et al. |
| 5,468,647 A | 11/1995 | Skold et al. |
| 5,482,839 A | 1/1996 | Ashihara et al. |
| 5,496,637 A | 3/1996 | Parham et al. |
| 5,543,054 A | 8/1996 | Charkoudian et al. |
| 5,559,041 A | 9/1996 | Kang et al. |
| 5,580,743 A | 12/1996 | Rittersdorf et al. |
| 5,591,645 A | 1/1997 | Rosenstein |
| 5,591,646 A | 1/1997 | Hudson et al. |
| 5,611,995 A | 3/1997 | De Zoeten et al. |
| 5,622,871 A | 4/1997 | May et al. |
| 5,633,168 A | 5/1997 | Glasscock et al. |
| 5,654,162 A | 8/1997 | Guire et al. |
| 5,656,503 A | 8/1997 | May et al. |
| 5,695,947 A * | 12/1997 | Guo et al. ..................... 435/11 |
| 5,714,389 A | 2/1998 | Charlton et al. |
| 5,726,010 A | 3/1998 | Clark |
| 5,726,013 A | 3/1998 | Clark |
| 5,728,352 A | 3/1998 | Poto et al. |
| 5,744,096 A | 4/1998 | Jones et al. |
| 5,786,164 A | 7/1998 | Rittersdorf et al. |
| 5,788,942 A | 8/1998 | Kitani et al. |
| 5,989,921 A | 11/1999 | Charlton et al. |
| 6,027,943 A | 2/2000 | Kang et al. |
| 6,107,045 A | 8/2000 | Koren et al. |
| 6,156,492 A | 12/2000 | Kobayashi et al. |
| 6,159,424 A | 12/2000 | Kauhaniemi et al. |
| 6,171,849 B1 * | 1/2001 | Rittersdorf et al. ....... 435/283.1 |
| 6,187,598 B1 | 2/2001 | May et al. |
| 6,194,225 B1 | 2/2001 | Oka et al. |
| 6,210,907 B1 | 4/2001 | Cha |
| 6,214,570 B1 | 4/2001 | Rittersdorf et al. |
| 6,228,660 B1 | 5/2001 | May et al. |
| RE37,437 E | 11/2001 | Friesen et al. |
| 6,352,862 B1 | 3/2002 | Davis et al. |
| RE37,701 E | 5/2002 | Bahar et al. |
| 6,406,920 B1 | 6/2002 | Davis et al. |
| 6,596,112 B1 | 7/2003 | Ditter et al. |
| 6,844,149 B2 | 1/2005 | Goldman |
| 6,881,581 B2 * | 4/2005 | Jones et al. ................... 436/71 |
| 7,087,397 B2 * | 8/2006 | Anaokar et al. ............... 435/11 |
| 7,195,921 B2 * | 3/2007 | Jones .......................... 436/71 |
| 7,220,595 B2 | 5/2007 | Nugent |
| 7,223,546 B2 | 5/2007 | Miki et al. |

| | | | |
|---|---|---|---|
| 7,238,519 B2 | 7/2007 | Bellet | |
| 7,476,548 B2 | 1/2009 | Blatt et al. | |
| 7,491,542 B2 | 2/2009 | Scheuringer | |
| 2003/0012905 A1 | 1/2003 | Zumbrum et al. | |
| 2003/0166291 A1 | 9/2003 | Jones et al. | |
| 2003/0175153 A1 | 9/2003 | Anaokar et al. | |
| 2004/0023400 A1 | 2/2004 | Tamura et al. | |
| 2004/0029293 A1 | 2/2004 | Nugent | |
| 2004/0126830 A1 | 7/2004 | Shull et al. | |
| 2004/0235182 A1 | 11/2004 | Jones et al. | |
| 2005/0124019 A1 | 6/2005 | Jones | |
| 2005/0147532 A1 | 7/2005 | Bellet | |
| 2005/0208609 A1* | 9/2005 | Jones et al. | 435/11 |
| 2005/0214161 A1 | 9/2005 | Gupta | |
| 2005/0221502 A1 | 10/2005 | Shindelman | |
| 2006/0051738 A1 | 3/2006 | Zweig | |
| 2008/0166745 A1 | 7/2008 | Khan et al. | |

FOREIGN PATENT DOCUMENTS

| | | |
|---|---|---|
| DE | 2727347 A1 | 12/1977 |
| DE | 3130749 A1 | 2/1983 |
| DE | 10204606 C1 | 10/2003 |
| EP | 0045476 A1 | 2/1982 |
| EP | 0146654 A2 | 7/1985 |
| EP | 0146654 A3 | 7/1985 |
| EP | 0176357 A1 | 4/1986 |
| EP | 0229982 A2 | 7/1989 |
| EP | 0229982 A3 | 7/1989 |
| EP | 0353570 A2 | 2/1990 |
| EP | 0353570 A3 | 2/1990 |
| EP | 0357400 A2 | 3/1990 |
| EP | 0357400 A3 | 4/1991 |
| EP | 0627627 A1 | 12/1994 |
| EP | 0 408 223 | 3/1995 |
| EP | 0740157 A2 | 10/1996 |
| EP | 0740157 A3 | 5/1998 |
| EP | 1 029 928 A2 | 8/2000 |
| EP | 1028319 A2 | 8/2000 |
| EP | 1029928 A3 | 9/2002 |
| EP | 1 357 383 A1 | 10/2003 |
| EP | 1028319 A3 | 1/2004 |
| GB | 2090659 A | 7/1982 |
| JP | 2-210265 A | 8/1990 |
| JP | 3-99268 A | 4/1991 |
| WO | WO 83/00931 A1 | 3/1983 |
| WO | WO 90/10869 A1 | 9/1990 |
| WO | WO 93/13856 A1 | 7/1993 |
| WO | WO 94/12879 A1 | 6/1994 |
| WO | WO 96/04556 A1 | 2/1996 |
| WO | WO 96/15453 A1 | 5/1996 |
| WO | WO 89/05458 A1 | 6/1998 |
| WO | WO 98/37416 A1 | 8/1998 |
| WO | WO 99/58966 A1 | 11/1999 |
| WO | WO 00/42434 A1 | 7/2000 |
| WO | WO 02/02796 A2 | 1/2002 |
| WO | WO 02/20142 A1 | 3/2002 |
| WO | WO 02/02796 A3 | 3/2003 |
| WO | WO 2004/025265 A2 | 3/2004 |
| WO | WO 2004/025265 A3 | 7/2004 |

OTHER PUBLICATIONS

International Search Report for International Application No. PCT/US03/01354.
Bachorik, et al. Precipitation Methods for Quantification of Lipoproteins. Methods in Enzymology. Academic Press, Inc. 1986;129:78-100.
Chandler, et al. The place of gold in rapid tests. IVD Technology. 2000; 6(2):37-49.
De Maat et al. Effect of fish oil and vitamin E on the cardiovascular risk indicators fibrinogen, C-reactive protein and PAI activity in healthy young volunteers. Fibrinolysis. 1994; 8(Suppl 2):50-52.
European search report Nov. 12, 2003 for Application No. 2022910.0.
European search report Sep. 5, 2005 for Application No. 03757364.9.
European search report dated Jan. 26, 2004 for Application No. 3025724.0.
European search report dated Nov. 17, 1994 for Application No. 92913182.9.
European search report dated Feb. 6, 1991 for Application No. 89308774.2.
European search report dated May 26, 2003 for Application No. 2013433.4.
European search report dated Jul. 24, 2003 for Application No. 2004339.4.
Fless, et al. Enzyme-linked immunoassay for Lp[a]. J Lipid Res. May 1989;30(5):651-62.
Grau, et al. Clinical and biochemical analysis in infection-associated stroke. Stroke. Sep. 1995;26(9):1520-6.
Hegele, R. Lipoprotein (a): an emerging risk factor for atherosclerosis. Can. J. Cardiol. 1989;5:263-265.
International search report dated Feb. 11, 2004 for PCT Application No. US2003/17792.
International search report May 24, 2005 for PCT Application No. IB2004/003704.
International search report Jul. 11, 1990 for PCT Application No. US1990/01249.
International search report dated Jan. 31, 1992 for PCT Application No. US1991/05004.
International Search Report dated Oct. 24, 2005 for PCT Application No. US05/11093.
International search report dated Dec. 8, 1989 for PCT Application No. US1989/03730.
International search report dated Apr. 2, 2008 for PCT Application No. US2008/000344.
International search report dated Jun. 23, 1998 for PCT Application No. US1998/02952.
International search report dated Jul. 14, 2006 for PCT Application No. US2005/045038.
International search report dated Aug. 28, 1992 for PCT Application No. US1992/04302.
International search report dated Sep. 17, 2003 for PCT Application No. US2003/10420.
International Search report from PCT/US2004/010001 dated Aug. 16, 2004.
Kuller, et al. Relation of C-reactive protein and coronary heart disease in the MRFIT nested case-control study. Multiple Risk Factor Intervention Trial. Am J Epidemiol. Sep. 15, 1996;144(6):537-47.
Litman, et al. An internally referenced test strip immunoassay for morphine. Clin. Chem. 1983;29(9):1598-1603.
Liuzzo, et al. The prognostic value of C-reactive protein and serum amyloid a protein in severe unstable angina. N Engl J Med. Aug. 18, 1994;331(7):417-24.
McNamara, et al. Immunoseparation method for measuring low-density lipoprotein cholesterol directly from serum evaluated. Clinical chemistry. 1995;41(2):232-240.
Mendall, et al. C reactive protein and its relation to cardiovascular risk factors: a population based cross sectional study. BMJ. Apr. 27, 1996;312(7038):1061-1065.
Nauck, et al. Analytical and clinical performance of a detergent-based homogeneous LDL-cholesterol assay: a multicenter evaluation. Clin Chem. Apr. 2000;46(4):506-14.
Paek, et al. Immunochromatographic membrane strip assay system for a single-class plasma lipoprotein cholesterol, exemplified by high-density lipoprotein cholesterol measurement. Biotechnol Bioeng. Jan. 20, 1999;62(2):145-54.
Seman, et al. Quantification of lipoprotein(a) in plasma by assaying cholesterol in lectin-bound plasma fraction. Clin Chem. Mar. 1994;40(3):400-3.
Sugiuchi, et al. Homogeneous assay for measuring low-density lipoprotein cholesterol in serum with triblock copolymer and alpha-cyclodextrin sulfate. Clin Chem. Mar. 1998;44(3):522-31.
Thompson, et al. Hemostatic factors and the risk of myocardial infarction or sudden death in patients with angina pectoris. European Concerted Action on Thrombosis and Disabilities Angina Pectoris Study Group. N Engl J Med. Mar. 9, 1995;332(10):635-41.

Tracy, et al. C-reactive protein and incidence of cardiovascular disease in older women: the rural health promotion project and the cardiovascular health study. Circulation. Feb. 1, 1996; 93(3):622, abstract 8. (Abstracts of the 36th annual conference on cardiovascular disease epidemiology and prevention, Mar. 13-15, 1996. Fairmont Hotel, San Francisco, CA.).

* cited by examiner

HIGH-DENSITY LIPOPROTEIN ASSAY DEVICE AND METHOD

This application claims priority to U.S. provisional application Ser. No. 60/371,093, filed Apr. 9, 2002, which is hereby incorporated by reference in its entirety.

FIELD OF THE INVENTION

The present invention relates to a method of determining the concentration of high density lipoprotein (HDL)-associated cholesterol in a blood-fluid sample, and a diagnostic assay device for carrying out the method.

BACKGROUND OF THE INVENTION

The amount of cholesterol present in the blood is known to be related to the risk of coronary artery disease. Cholesterol circulates in the blood predominantly in protein-bound form. The proteins which transport cholesterol are the lipoproteins, which are subdivided into three classes based on their density. The very-low density lipoproteins (VLDL) are triglyceride-rich lipoproteins which are synthesized in the liver and ultimately converted to low-density lipoproteins (LDL), which transport most of the plasma cholesterol in humans. The high-density lipoproteins (HDL) are lipoproteins which are involved in the catabolism of triglyceride-rich lipoproteins, and in the removal of cholesterol from peripheral tissues and transport to the liver. An inverse relationship between serum HDL levels and risk of coronary disease has been established. In particular, if the proportion of serum cholesterol associated with HDL is low, the risk of coronary disease is increased.

In view of the importance of relative serum cholesterol levels in risk assessment and management of atherogenic disease, considerable effort has been spent screening large populations of both normal and high-risk individuals for serum levels of HDL, LDL, as well as total cholesterol and triglycerides. The effectiveness of treatments of high-risk individuals has been monitored by regular testing of serum levels of cholesterol in the various lipoprotein compartments.

One method for specific HDL cholesterol testing is based on the selective precipitation of non-HDL lipoproteins in serum by a polyanionic compound, such as dextran sulfate, heparin, or phosphotungstate, typically in the presence of a group II cation, such as $Mg^{2+}$, $Mn^{2+}$, or $Ca^{2+}$. The specificity and degree of precipitation are dependent on a variety of factors, including the type and concentration of the precipitating reagent. In general, the order of precipitation of serum cholesterol particles, with increasing concentration of polyanion, is VLDL, LDL, and HDL. HDL usually remains soluble at concentrations of heparin or dextran sulfate which completely precipitate lower density particles, although minor apoE species of HDL may be co-precipitated with lower density particles. By selective precipitation of lower density particles, HDL serum cholesterol levels can be determined.

In a typical lipid assay procedure, a small volume of blood is drawn and centrifuged to produce a clear plasma or serum sample fluid. The sample fluid is then aliquoted into several assay tubes, for determination of (a) total serum cholesterol, (b) triglycerides, and (c) HDL cholesterol. The HDL sample is precipitated, as above, and the lower density particles are removed by filtration or centrifugation prior to cholesterol detection. The samples are then reacted with an enzyme mix containing cholesterol esterase, cholesterol oxidase, peroxidase, and a dye which can be oxidized to a distinctly colored product in the presence of $H_2O_2$. The tubes may be read spectrophotometrically, and the desired total, HDL and LDL cholesterol values determined.

Despite the accuracy and reliability which can be achieved with the liquid-phase cholesterol assay just described, the assay has a number of limitations for use in widespread screening. First, the method uses a venous blood sample, requiring a trained technician to draw and fractionate the blood sample, and aliquot the treated blood to individual assay tubes. At least one of the sample tubes (for HDL determination) must be treated with a precipitating agent and further processed to remove precipitated material. Although some of these procedures can be automated, analytical machines designed for this purpose are expensive and not widely available outside of large hospitals.

Co-owned U.S. Pat. Nos. 5,213,964, 5,213,965, 5,316,196 and 5,451,370, each of which is incorporated herein by reference, disclose methods and assay devices which substantially overcome many of the above-mentioned problems associated with liquid-assay procedures for measuring serum cholesterol levels. In one embodiment, the device is designed for measuring the concentration of HDL-associated cholesterol in a blood sample also containing LDL and VLDL particles. The device includes a sieving matrix capable of separating soluble and precipitated lipoproteins as a fluid sample migrates through the matrix. A reservoir associated with the matrix is designed to release a soluble precipitating agent, for selectively precipitating LDL and VLDL, as fluid sample is drawn into and through the matrix. This allows HDL separation from the precipitated lipoproteins, based on faster HDL migration through the sieving matrix. The fluid sample, thus depleted of non-HDL lipoproteins, then migrates to a test surface where it is assayed for cholesterol.

The above-referenced devices, while representing an advance over liquid-phase assays, present the possibility of contamination of the flow transport path with the precipitating reagents. Such reagents could interfere with HDL quantification, or with other assay chemistry taking place on other regions of a multi-assay device. The present invention addresses and overcomes these problems.

Further methods and devices for measuring HDL cholesterol in blood samples are disclosed in EP 0408223 and EP 0415298 (Rittersdorf et al.), which describe a continuous assay method carried out on a test strip comprising the following steps and corresponding elements. The blood sample is applied to a separation layer for separating cellular blood constituents. Driven by capillary forces or gravity, the sample flows through a further carrier containing soluble precipitating agents, which, after dissolving in the serum sample, precipitate non-HDL lipoproteins contained in the sample. In a further carrier, the precipitated constituents, above, are filtered from the serum sample to prevent their interference with later HDL quantification. In the same carrier, the sample is transported to a position adjacent the HDL-quantification carrier, and is stored until the HDL quantification step is to be started. Finally, the sample is transferred to an HDL quantification layer, where HDL cholesterol in the serum sample is quantified by an enzymatic reaction.

A disadvantage of this assay design is that the carrier functioning as a reservoir allows migration of the precipitated constituents or soluble reagents into the sample, which can interfere with HDL quantification. In addition, during the storage of the serum sample, HDL can be trapped by adhering to the carrier fibers, precipitating reagents can cause further undesired reactions, and the carrier can become clogged by the drying serum sample.

U.S. Pat. No. 5,135,716 (Thakore) discloses additional devices and methods for HDL quantification in a blood fluid sample. In these devices, the fluid sample flows continuously, though an unbroken path, from an inlet well to a carrier for HDL quantification. Accordingly, the ability to control sample volume entering the HDL test carrier, and to control environmental conditions for the HDL assay, is limited. Nor do the devices provide for simultaneous assay of various analytes from a single fluid sample.

It is therefore the object of the present invention to provide a HDL assay device and method which overcome the above-noted prior art disadvantages.

SUMMARY OF THE INVENTION

In one aspect, the invention provides an assay device for measuring serum cholesterol associated with high-density lipoproteins (HDL) in a blood fluid sample which also contains low density lipoproteins (LDL) and/or very low density lipoproteins (VLDL). The device comprises:

(i) a plurality of porous elements through which such a blood fluid sample can flow in sequence by capillary action and/or gravity, wherein the plurality of elements comprises: a sample distribution matrix; an HDL test pad, downstream of said matrix, in which HDL concentration can be assayed; and, upstream of the HDL test pad, an element containing an immobilized reagent effective to selectively bind and remove non-HDL lipoproteins from the fluid sample.

The device further comprises: (ii) mounting means effective to adjust the device between (a) a sample-distribution position, wherein the HDL test pad is not in fluid communication with the sample distribution matrix, and (b) a test position, wherein the HDL test pad and distribution matrix are in fluid communication with each other.

Preferably, the immobilized reagent comprises a polyanionic reagent, more preferably a sulfonated polysaccharide. In one embodiment, the immobilized reagent is immobilized to a first sample collection region within the sample distribution matrix, which is placed in fluid communication with the HDL test pad when the device is in the test position. In another embodiment, the immobilized reagent is immobilized to a porous reagent pad located downstream of the distribution matrix and upstream of the HDL test pad, which reagent pad is placed in fluid communication with the HDL test pad when the device is in the test position. The reagent pad may be attached to the HDL test pad.

Preferably, the device further comprises: a sieving pad, upstream of and contacting the sample distribution matrix, effective to remove cellular components from the blood fluid sample, and a cassette body containing the sieving pad and further comprising a well for containing the blood fluid sample, the well being in fluid communication with the sieving pad and sample distribution matrix.

Preferably, the device also includes a reaction bar to which the HDL test pad is attached, and the above-noted mounting means is effective to adjust the relative positions of the reaction bar and cassette body between the sample-distribution position and the test position. The mounting means may also attach the reaction bar to the cassette body. Preferably, the mounting means is further effective to transfer the device from the test position to a position in which the HDL test pad is not in fluid communication with the sample distribution matrix.

In one embodiment, the sample-distribution matrix contains additional sample collection regions, and the reaction bar comprises additional test pads, such that the additional pads are brought into fluid communication with the additional sample collection regions when the device is transferred to the test position.

Typically, the HDL test pad contains reagents which, in the presence of HDL cholesterol, produce a detectable change in the test pad, which, in one embodiment, is an optically detectable change. The HDL assay pad may comprise a biosensor, which is preferably effective to electrochemically measure production of oxygen or hydrogen peroxide which is dependent on HDL-associated cholesterol concentration within the assay pad.

In one embodiment, the reagent pad comprises a porous polymeric membrane. In a preferred embodiment, where the immobilized reagent is an anionic reagent, such as a sulfonated polysaccharide, the polymeric membrane contains cationic surface groups. In a further embodiment, each of the HDL test pad and reagent pad is a porous polymeric membrane, and the membranes are laminated together.

In another aspect, the invention provides an assay device for measuring serum cholesterol associated with high-density lipoproteins (HDL) in a blood fluid sample also containing low density lipoproteins (LDL) and/or very low density lipoproteins (VLDL), the device comprising: a sample distribution matrix for distributing the blood fluid sample; a reagent pad containing an immobilized reagent effective to selectively remove non-HDL lipoproteins from the fluid sample; and a HDL test pad in which HDL concentration can be assayed, which is in fluid communication with the reagent pad; wherein the reagent pad may be brought into fluid contact with the sample matrix. Preferably, the reagent pad can be brought into fluid contact with the sample matrix from a position in which it is not in fluid contact with the sample matrix.

The immobilized reagent preferably comprises a sulfonated polysaccharide, and the reagent pad preferably comprises a porous polymeric membrane having cationic surface groups.

In a related aspect, the invention provides a method of measuring serum cholesterol associated with high-density lipoproteins (HDL) in a blood fluid sample also containing low density lipoproteins (LDL) and/or very low density lipoproteins (VLDL). The method comprises:

(a) contacting such a sample with an absorptive sample distribution matrix, wherein the sample distribution matrix is one of a plurality of porous elements contained within an assay device, through which the sample can flow in sequence by capillary action and/or gravity, wherein the plurality of elements further includes: an HDL test pad, downstream of the sample distribution matrix, in which HDL concentration can be assayed; and, upstream of the HDL test pad, an element containing an immobilized reagent effective to selectively bind and remove non-HDL lipoproteins from the fluid sample;

(b) contacting the sample with the element containing the immobilized reagent;

(c) placing the matrix in fluid communication with the HDL test pad, whereby the sample is transferred from the element to the HDL test pad; and (d) determining the content of HDL lipoproteins in the blood fluid sample.

In accordance with the method, prior to step (c), the matrix is not in fluid communication with the HDL test pad.

Preferably, the immobilized reagent-containing element is a porous reagent pad, located downstream of the distribution matrix and upstream of the HDL test pad, which reagent pad is placed in fluid communication with the HDL test pad in step (c). In one embodiment of the method, the matrix is not in fluid communication with the reagent pad prior to step (b). Preferably, upon contacting the matrix with the reagent pad in step (b), the reagent pad is in simultaneous fluid communication with the HDL test pad. The reagent pad may be attached to the HDL test pad.

In another embodiment, the immobilized reagent-containing element is the matrix, such that the contacting of steps (a) and (b) occurs concurrently.

In yet another embodiment, the immobilized reagent is contained within a sieving matrix upstream of and contacting the sample distribution matrix, such that the contacting of steps (a) and (b) occurs in reverse order.

Preferably, the method further comprises the step of breaking the fluid communication between the matrix and the test pad, when a desired amount of sample has been transferred.

In preferred embodiments of the method, the immobilized reagent comprises a sulfonated polysaccharide, and the reagent pad comprises a porous polymeric membrane having cationic surface groups.

The indication of HDL cholesterol at the test pad may be optically detectable. The HDL test pad may also comprise a biosensor. The biosensor is preferably effective to electrochemically measure production of oxygen or hydrogen peroxide which is dependent on HDL-associated cholesterol concentration within the test pad.

These and other objects and features of the invention will become more fully apparent when the following detailed description of the invention is read in conjunction with the accompanying drawings.

DETAILED DESCRIPTION OF THE INVENTION

I. Definitions

The terms below have the following meanings unless indicated otherwise.

A first element is in "fluid communication" or "fluid contact" with a second element when a fluid is able to travel from the first to the second element, via a path of contiguous solid elements, under the impetus of capillary action and/or gravity. The first and second elements may be in direct contact, or elements through which the fluid can pass may be intervening, as long as the first and second elements are connected by a contiguous path of solid elements.

An element is "not in fluid communication" with another element when a fluid is not able to travel from one element to the other via capillary action and/or gravity. Typically, the elements are physically separated, i.e. spaced apart.

A "pad", such as a reagent pad or assay pad, as used herein, may comprise any material, such as a porous membrane or fibrous strip, which can contain impregnated or immobilized reagents and through which fluid can move via capillary action and/or gravity.

II. Assay Device

Figure 2:
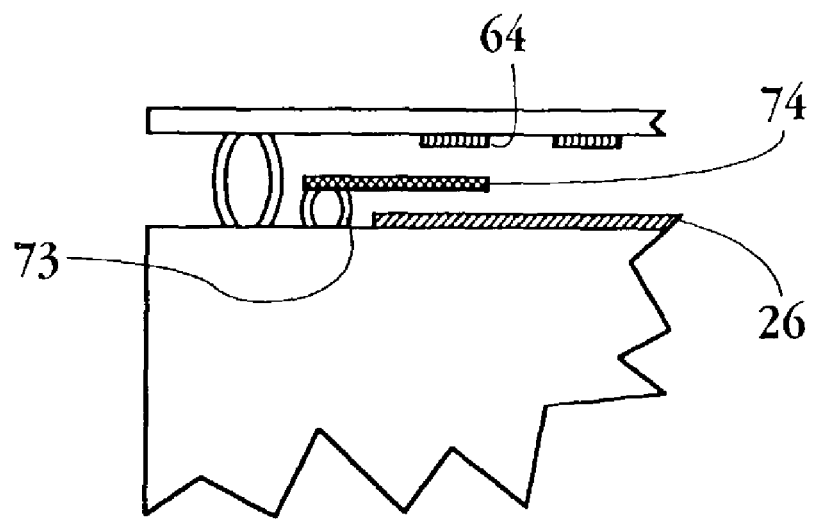
Figure 3:
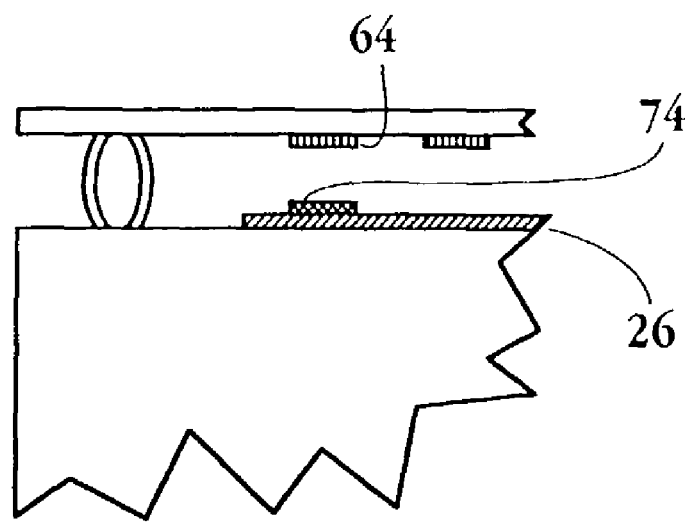
Figure 4:
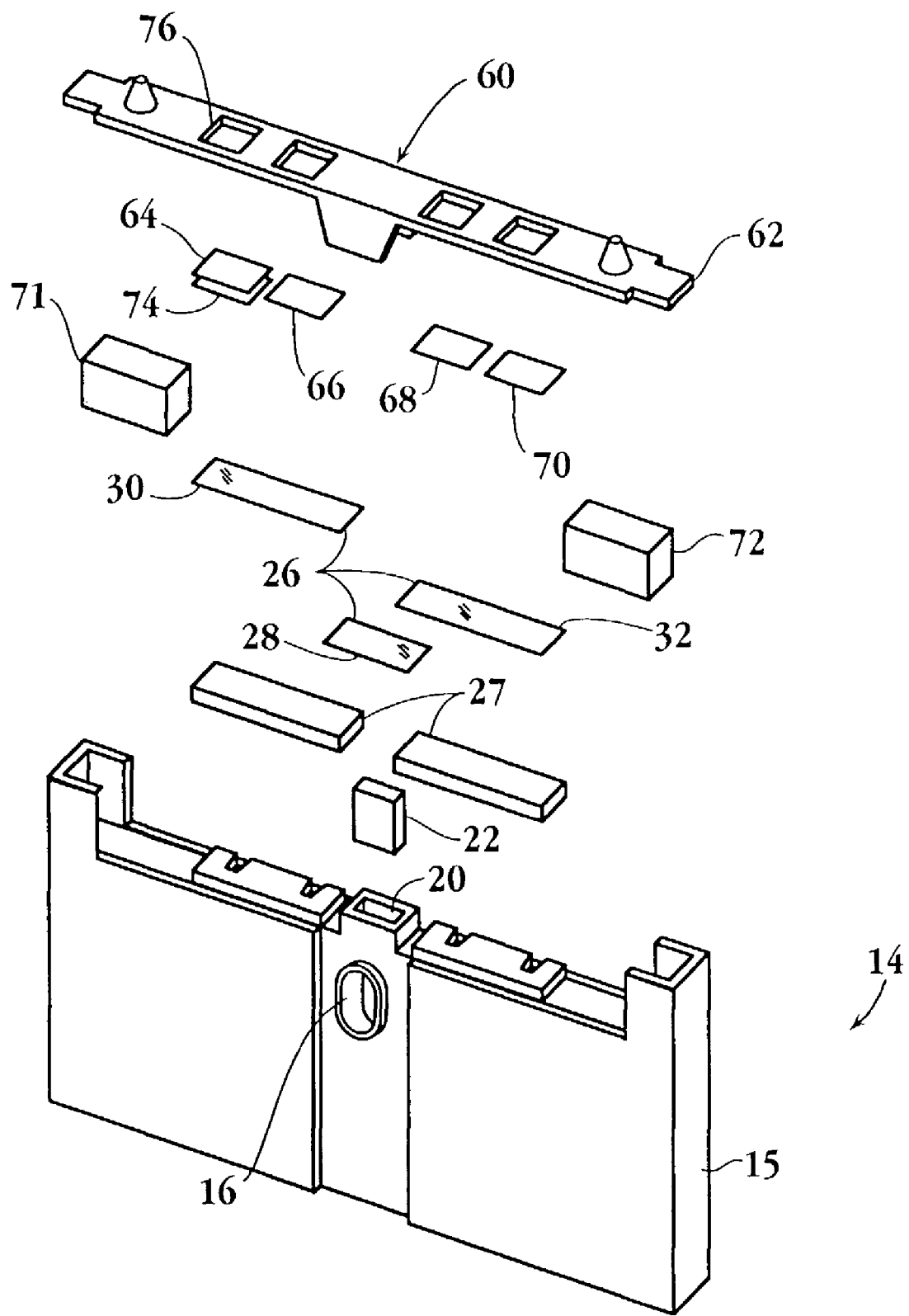
FIG. 4 is a perspective view, in exploded form, of a multi-analyte assay device constructed in accordance with one embodiment of the invention.

FIGS. 1-4 illustrate various embodiments of a multiple-analyte assay device 14 constructed in accordance with the present invention, with FIG. 4 shown in exploded format. The device is designed particularly for determining serum cholesterol associated with HDL (also referred to as HDL-associated cholesterol or simply HDL cholesterol) using a small volume of blood sample, typically between 10-50 µl of blood. Other assays, such as total cholesterol or triglyceride level, can be determined simultaneously from the same sample. Determination of HDL-associated cholesterol may also be referred to simply as determination of HDL or an HDL assay.

Figure 1:
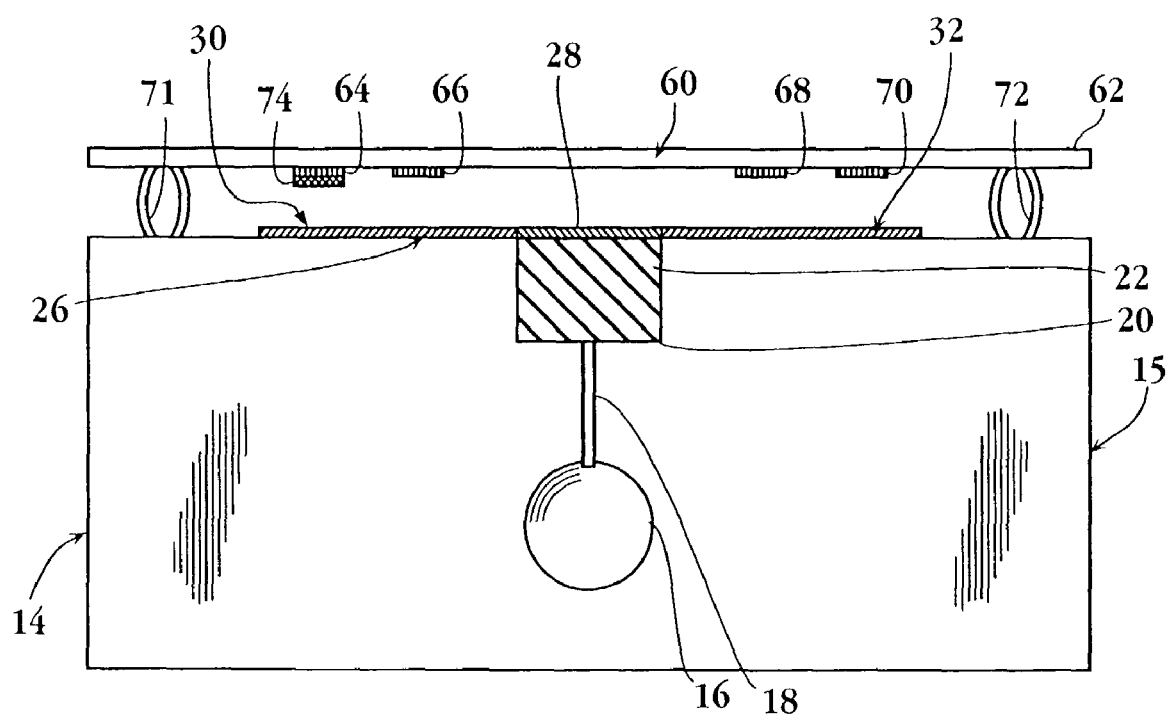
FIGS. 1-3 are side views of multi-analyte assay devices constructed in accordance with various embodiments of the invention, with FIGS. 2 and 3 showing partial views.

The apparatus includes a main body or support 15 which defines a well 16 dimensioned and sized to receive a quantity of a blood sample, typically between about 25-50 µl. The well is in fluid contact with a sieving pad 22, which may be carried in a notched region 20 formed in the upper edge of the support. The fluid contact may be direct, or as in the device shown in FIG. 1, provided by a capillary conduit 18 formed in the plate at the base of the well. The support is preferably a plastic plate, with the well, notched region and/or capillary formed by standard molding or machining methods.

Sieving pad 22 carried in region 20 functions to partially remove large particulate matter (including blood cells) as the sample migrates through the pad matrix in a bottom-to-top direction as shown in the figure. Pad 22 is preferably formed of a glass fibrous matrix of material designed to draw aqueous fluid by surface wetting, and to retard the movement of blood cells as the blood sample is drawn through the matrix. One exemplary pad is a glass fiber filter, such as a GF/D or PD008 filter supplied by Whatman, having a packing density of about 0.16 g/cm$^3$, and a thickness of about 1 mm. The pad is dimensioned to absorb a defined volume of sample fluid, preferably between about 15-25 µl. Sieving pad 22 may additionally contain red blood cell capture reagents, such as lectins, antibodies specific for red blood cell surface membrane proteins, thrombin, or ion exchange agents. In one embodiment, the pad may contain immobilized reagents for removal of non-HDL lipoproteins, as described further below.

The sieving pad, 22, in turn, contacts an elongate strip or sample distribution matrix 26 which extends along the upper edge of plate 15. This strip may also be supported by foam cushions 27 or other supports, as shown in FIG. 4. Matrix 26 serves to distribute sample fluid from a central sample-application region 28, which is in fluid contact with pad 22, to sample-collection regions such as 30, 32 within the matrix. The matrix is preferably formed of glass fibers. The packing density and thickness of the matrix are such as to absorb and distribute volumes of sample fluid, e.g., 10-25 µl, supplied to the sample-application region of the strip to the sample-collection regions of the strip. The matrix has a preferred packing density between about 0.16 g/cm$^3$ and 4.0 g/cm$^3$. One exemplary strip material is a F-165-25A glass fiber filter available from Whatman, having a packing density of about 0.2 gm/cm$^3$ and a thickness of about 0.12 mm.

Device 14 also includes a reaction bar 60 composed of an elongate support 62, and multiple wettable, absorbent reaction test pads 64, 66, 68 and 70, carried on the lower surface of the support, as shown. Support 62 is transparent or has windows, e.g. window 76 (FIG. 4), which allow the pads to be viewed through the support. These windows may be transparent materials or simply openings in the support. The reaction test pads in the reaction bar are attached to the support by a transparent or translucent adhesive material, or by sonic welding or other suitable bonding method. Each test pad used in a particular assay contains analyte-dependent reagents effective to produce an analyte-dependent change in the pad which can be detected in a known manner, as described further below. All or any integral subset of the test pads may be employed in a particular assay.

Desirably, the reaction test pads are porous polymer membranes, preferably having a thickness of about 100-150 µm and side dimensions of about 3 mm. The absorption volume of each pad is preferably between about 0.5-1.0 µl. In one embodiment, some or all of the reaction pads are asymmetric membranes; that is, membranes having a porosity gradient across the thickness of the membrane.

The reaction bar is mounted on support 15 by mounting means effective to (a) maintain the device in a sample-distribution position, wherein the test pad and, in one embodiment, the reagent pad (described further below), are spaced apart from the sample distribution matrix, and to (b) transfer the device to a test position, where the test pad, reagent pad, if present, and sample distribution matrix are all in fluid communication. The mounting means can also be used to break such fluid communication after a desired amount of sample has entered the test pads, and/or after a determined contact time, by transferring the device from the test position to a position in which the test pads are not in fluid communication with the sample distribution matrix (which may be the same as the "sample-distribution" position). Such transferring can be controlled by monitoring the reflectance at the top surface of the test pad, which reflects extent of wetting, as described in co-owned U.S. Pat. No. 5,114,350. Alternatively, when the absorption capacity and rate of sample uptake of the pad material are known, the quantity of sample can be controlled with sufficient accuracy simply by using a predetermined contact time.

The mounting means can include, for example, a pair of resilient members, such as elastomeric blocks 71, 72, which act to bias the test pad and, in one embodiment, the reagent pad toward a non-transfer or sample-distribution position, at which the pads are spaced apart from the sample distribution matrix. By compression or release of the resilient members, fluid communication between sample distribution matrix 26 and HDL test pad 64 and/or reagent pad 74 (described further below) can be selectively established and separated. The fluid communication may be via direct contact or through an intermediate element. The support blocks could be compressed by means of springs or a piston-like action. Alternatively, external mechanical devices could engage the main body 15 and/or support 62 and move one towards the other. Such devices may include conventional components such as clamps, pistons, stepper motors, worm gears, or the like. An exemplary system is the CHOLESTECH LDX® Analyzer, a self-contained, automated analyzer advantageous for use with assay devices such as described herein.

Provided in the HDL assay flow path, upstream of the HDL test pad, is an element having immobilized thereto a polyanionic reagent effective to bind, and remove from the fluid sample, non-HDL lipoproteins. This element may be the sieving pad or the sample distribution matrix. Preferably, a separate reagent pad 74 having such immobilized reagent is provided between the sample distribution matrix and HDL test pad. This reagent pad may be affixed to the sample distribution matrix, as shown in FIG. 3, or, more preferably, to the test pad used for assaying HDL, as shown in FIGS. 1 and 4. Immobilized binding reagents may be present in any or all of elements 22, 26, and 74; preferably, they are limited to reagent pad 74.

Such a reagent pad 74 may also be supported in a substantially coplanar position between the HDL test pad and a sample collection region of matrix 26, as shown in FIG. 2. For example, a compressible support element 73 could support reagent pad 74 above the matrix, such that movement of the reaction bar towards the main body (or vice versa) would bring these areas into fluid communication, preferably first bringing test pad 64 into fluid communication with the upper surface of reagent pad 74, and then bringing the lower surface of the reagent pad into fluid communication with the sample distribution matrix. As noted above, the fluid communication may be by direct contact, as illustrated in the Figures, or through an intermediate element.

The reagent pad preferably has a thickness of about 100-150 µm, side dimensions of about 3×6 mm, and an absorption volume of about 0.5-1.0 µl. It contains an immobilized reagent effective to selectively remove LDL and VLDL particles from the fluid sample. The reagent may be, for example, an antibody, or preferably a polyanionic LDL- and VLDL binding reagent. Such reagents, which are known in the art, include sulfonated polysaccharides, heparin, and phosphotungstate, in the presence or absence of a group II cation, such as $Mg^{2+}$, $Mn^{2+}$, or $Ca^{2+}$. A preferred reagent is a sulfonated polysaccharide, such as dextran sulfate, having a typical molecular weight of 50,000 to 500,000 daltons, optionally in combination with magnesium acetate or chloride, buffered to maintain neutral pH.

The reagent pad is effective to entrap bound non-HDL lipoproteins within the reagent pad and prevent them from entering HDL test pad 64. Because the binding reagents are immobilized to the carrier, and not soluble in the fluid sample, migration of precipitated sample constituents, and precipitating reagent, into the HDL test pad is avoided.

In a preferred embodiment, reagent pad 74 is composed of a porous polymeric membrane, having pore sizes of about 1µ or less. In one embodiment, the polyanionic reagent, e.g. dextran sulfate, is immobilized by electrostatic forces and/or covalently to a membrane having positively charged surface groups. An exemplary material for this purpose is a nylon membrane having surface quaternary ammonium groups, such as an AM080 membrane provided by Cuno Corp. (Meridian, Conn.). Other commercial polymeric membranes having a cationic surface include IMMOBILON™-Ny+ (Millipore Corp., Bedford, Mass.), ZETABIND® (also from Cuno Corp.), GENESCREEN® (NEN/DuPont, Boston, Mass.), HYBOND™ N+ (Amersham, Piscataway, N.J.) and POSIDYNE® (Pall Corp., Glen Cove, N.Y.).

U.S. Pat. No. 5,543,054 (Charkoudian et al.) describes a method for covalently binding negatively charged carbohydrates to a membrane having reactive moieties in proximity to positively charged moieties on its surface. The membrane is, for example, a porous polymer, e.g. polytetrafluroethylene, polyvinylidene fluoride, polyester, polyamide, polycarbonate, polypropylene, polymethylmethacrylate, polymethacrylate, polysulfone, or polystyrene, coated with Hercules R-4308, a polyamido-polyamine epichlorohydrin resin.

In the case of a positively charged membrane, as described above, the membrane may be impregnated with a solution of polyanion via an automated dispensing process and dried. The membrane may also be impregnated with divalent cation. Alternatively, the reagent may be immobilized onto small particles which are then applied to a suitable membrane.

For immobilization of reagent onto glass fibers, in embodiments in which binding reagent is immobilized to the sieving matrix and/or sample distribution matrix, the fibers may be first coated with a cationic polymer as described above. Alternatively, the glass fibers may be functionalized with a reagent containing a siloxane group and a cationic group (e.g., 3-(triethoxysilyl)propyltrimethylammonium chloride or similar reagents), as is known in the art for functionalization of silica-based surfaces.

A polyanionic binding reagent can also be immobilized to a membrane or other substrate, such as a fibrous substrate, by covalent attachment. Various chemical methods of covalently attaching polysaccharides to various substrates are known in the art. (See e.g. U.S. Pat. Nos. 4,744,899 (Tani et al.), 6,281, 202 and 6,008,203 (Magnani et al.), 6,204,254 (Nelson et al.), 6,060,525 (Slingsby et al.), 5,919,523 (Sundberg et al.), and 5,811,532 (House)). For example, a hydroxyl-containing surface may be modified with epichlorohydrin to produce an epoxidized surface, which reacts with hydroxyl groups in the polysaccharide. Alternatively, the polysaccharide can be modified to contain electrophilic groups, such as epoxides, esters or aldehydes, which can then react with an amino- or thiol-containing surface. For attachment to glass surfaces or glass fibers, as well as other hydroxyl-containing surfaces, functionalized silane reagents, such as aminoalkyl or hydroxyalkyl-trialkoxysilanes, are particularly useful.

In one embodiment, reagent pad 74 consists of a single membrane. The invention also contemplates the use of multiple stacked membranes, i.e. up to about six, where at least one and preferably each membrane contains reagents for binding of non-HDL lipoproteins, for reagent pad 74.

In one embodiment, test pad 64 is also a polymeric membrane, containing reagents for assaying HDL level. If desired, HDL assay reagents, such as peroxidase, may be immobilized to the test pad membrane, according to well known methods for enzyme immobilization. (See e.g. U.S. Pat. No. 4,999,287; U.S. Pat. No. 5,419,902; Blum, L. J. et al., *Anal. Lett.* 20(2):317-26 (1987); Kiang, S. W. et al., *Clin. Chem.* 22(8): 1378-82 (1976); Guilbault, G. G., Ed., *Modern Monographs in Analytical Chemistry, Vol. 2: Analytical Uses of Immobilized Enzymes* (1984); Torchilin, V. P., *Progress in Clinical Biochemistry and Medicine, Vol. 11: Immobilized Enzymes in Medicine* (1991).) In another embodiment, a reagent, such as catalase, which is effective to decompose any generated hydrogen peroxide that might diffuse downward from test pad 64, may be included in reagent pad 74.

In a preferred embodiment, where two attached polymeric membranes are employed for test pad 64 and reagent pad 74, respectively, the appropriate reagents are impregnated or immobilized, and the membranes are processed as a two-membrane layer for incorporation into the assay device during manufacture.

In a further embodiment, the HDL assay pad comprises a biosensor, as described, for example, in PCT Pubn. No. WO 9958966 (Dobson et al.), which is incorporated herein by reference. This document discloses a microscale biosensor device, comprising a conducting surface, a layer of dielectric material overlying the conducting surface, and a plurality of pores extending through the dielectric layer. Each of the pores contains a biopolymer in contact with the conducting surface, and can act as a microelectrode, converting a chemical response into an electrical signal. In use, a fluid containing an analyte to be assayed is applied to the pores so as to be in contact with the biopolymer. In the present HDL assay device, this is achieved when reagent pad 74, containing sample fluid, is placed or maintained in fluid communication with the HDL assay pad; that is, the pore-containing surface of the biosensor.

The biopolymer within the microelectrode pores is typically an enzyme, such as, for the measurement of HDL-associated cholesterol, cholesterol oxidase. Cholesterol is oxidized by cholesterol oxidase to the corresponding ketone, liberating hydrogen peroxide, which can then be converted to water and oxygen by the enzyme peroxidase. Either oxygen or hydrogen peroxide can then be measured electrochemically. Electrochemical methods that may be used include amperometric methods, as in the Clark oxygen electrode, which measures current produced by reduction of oxygen or oxidation of hydrogen peroxide, or voltammetric methods. The use of cyclic voltammetry at microelectrodes has been described for measurement of various analytes (see e.g. R. J. Forster, *Chem. Soc. Rev.* 289-297 (1994)), such as dopamine (Pihel et al., *Anal. Chem.* 68(13) 2084-9 (1996) and fullerenes (Soucaze-Guillous et al., *Anal. Chem.* 65(6):669-72 (1993)) as well as hydrogen peroxide (Horrocks et al., *Anal. Chem.* 65(24):3605-14 (1993); Nowall et al., *Electroanalysis* 9(2): 102-9 (1997); Dequaire et al., *J. Am. Chem. Soc.* 124(2):240-53 (2002)).

III. Assay Method

In operation, a blood sample is placed into well 16, and is imbibed through sieving pad 22, where large particulates, including red blood cells, are removed, and thence into sample distribution matrix 26. These steps take place while the device in a "sample-distribution" stage, such that the sample distribution matrix is not in fluid communication with the test pads, nor, in certain embodiments (e.g. FIGS. 1-2), with the reagent pad 74.

At some point prior to contacting the test pads, sample serum contacts immobilized binding reagent, which may be contained in the sieving matrix, the sample distribution matrix, or, more preferably, in a separate reagent pad, such that non-HDL lipoproteins are bound to the respective carrier. The device is thus effective to remove non-HDL lipoproteins from the serum, while allowing passage of serum containing liquid-phase HDL to HDL test pad 64. In one embodiment, this removal occurs while the device is in the sample distribution position; i.e. where the reagent is immobilized to the sieving pad, to the sample distribution matrix, or, preferably, to a separate reagent pad which is in fluid communication with these elements (e.g. FIG. 3).

In a further preferred embodiment, the reagent is immobilized to a reagent pad 74 which is not in fluid communication with the sieving matrix or sample distribution matrix during the sample-distribution stage, e.g. as shown in FIGS. 1-2 and 4. One advantage of the embodiments of FIGS. 1-4, which employ a separate reagent pad, is that the sample distribution matrix and upstream elements do not contain non-HDL binding reagents; such reagents are present only in reagent pad 74. Therefore, the possibility of interference from these reagents, in assays of analytes other than HDL, is eliminated.

When the serum sample reaches the sample-collection sites, such as sites 30 and 32 adjacent the ends of matrix 26, the device is adjusted to a test position, preferably by moving reaction bar 60, to place the test pads 64, 66, 68, and/or 70 and, in the embodiments of FIGS. 1-2 and 4, reagent pad 74, in fluid communication with the matrix. In this position, sample fluid in the matrix is drawn into the test pad(s) by capillary flow. The reaction bar is held at this position until a desired degree of wetting of the test pad(s) is achieved. The bar is then moved, if desired, to break fluid communication between the sample distribution matrix and the test pad(s), when a desired amount of sample fluid has entered the test pad(s), and/or after an appropriate contact time.

In embodiments of the device in which reagent pad 74 is positioned between test pad 64 and sample-distribution matrix 26 but affixed to neither (e.g. FIG. 2), respective movement of the reaction bar and main body toward each other, typically by moving the reaction bar downward, places these three areas in fluid communication, preferably by first placing test pad 64 in fluid communication with reagent pad 74, to approximate the arrangement of elements shown in FIGS. 1 and 4, and then, by further movement, placing the reagent pad in fluid communication with the sample distribution matrix. Contact is maintained until a desired degree of wetting is achieved, as described above.

During operation, in embodiments such as illustrated in FIGS. 1-2 and 4 (further characterized in that binding reagents are limited to element 74), as sample fluid passes through the HDL assay path, comprising pads 74 and 64, its leading edge passes in an upward direction through pad 74, where non-HDL lipoproteins react and are entrapped, and directly to adjacent assay pad 64, where HDL reacts with the assay reagents therein, for measurement of HDL-associated cholesterol. Further portions of sample continue to be in contact with pad 74 during this time, and proceed from pad 74 to pad 64 in a like manner, until the absorption capacity of pad 64 is reached. Accordingly, quantification of HDL-associated cholesterol in test pad 64 occurs concurrently with the binding reaction taking place in reagent pad 74. Preferably, the volume of sample fluid transferred to the HDL assay path (comprising pads 74 and 64) from the sample distribution matrix is equal to or greater than the absorption capacity of test pad 64, and less than or equal to the combined absorption capacity of test pad 64 and reagent pad 74.

In these embodiments, when the sample fluid contacts reagent pad 74 containing the immobilized binding reagents, the latter is in direct contact with HDL test pad 64, thus limiting the temporal contact of the blood sample with the binding reagents prior to the HDL assay reaction. Sample preparation and HDL evaluation are thus carried out in separate steps, where sample preparation includes, for example, filtering of cellular blood components and, optionally, temporary storage of the blood sample and adaptation of the blood sample to such test requirements or conditions as temperature, pressure and environmental atmosphere. Because the temporal contact of the blood sample with the different reagents is reduced, any chemical interference with the HDL evaluation is prevented. Because the reagents are immobilized, they are unlikely to migrate from the reagent pad into adjoining elements. If desired, the assay can be interrupted for a desired time after the sample application and removal of cellular components, but prior to contact with binding reagents, e.g. to adjust the surrounding atmosphere or adapt the environmental temperature to support the testing. This is accomplished by maintaining the device in the sample-distribution position. To this end, the sample distribution matrix is designed to additionally serve as a reservoir, if needed.

The HDL test pad contains reagents for quantification of HDL-associated cholesterol. Preferably, these include cholesterol esterase, for releasing free cholesterol from HDL, cholesterol oxidase, for producing $H_2O_2$ by reaction with free cholesterol, peroxidase, and a coupled dye system which is converted, in the presence of peroxidase and $H_2O_2$, to a distinctively colored signal reaction product. The test pad may also comprise a biosensor effective to electrochemically quantify $H_2O_2$ and/or $O_2$, as described above.

The remaining test pads also contain assay reagents which produce a change in the pad which can be detected optically, either visually or by a detector, in a known manner. In preferred embodiments of the current device and method, the non-HDL binding reagents are located in reagent pad 74, and not in the sample distribution matrix or sieving matrix Therefore, the possibility of interference from these reagents, in assays of analytes other than HDL, is eliminated.

Preferably, each of the assay pads contains reagent components for producing $H_2O_2$ via reaction of the analyte with an enzyme; the $H_2O_2$ subsequently converts a substrate reagent to a colored signal reaction product, or is measured electrochemically, as described above. Enzymatic color reactions which employ a variety of substrate-specific oxidases, for enzymatic generation of $H_2O_2$, and subsequent oxidation of a dye to form a colored reaction product, are well known.

A device having four or more reaction pads can be used to simultaneously measure HDL cholesterol (HDL), glucose, total cholesterol (TCh), and triglyceride lipid (TG). Each pad contains the above-described common pathway components (peroxidase and a coupled dye system) such that generated $H_2O_2$ produces a distinctly colored signal reaction product. The total cholesterol test pad, which is exposed to serum without exposure to a precipitating or binding reagent, and the HDL test pads each include, in addition to the common pathway components, cholesterol esterase, for releasing esterified cholesterol in free-cholesterol form from serum lipoproteins, including HDL, LDL, and VLDL particles, and cholesterol oxidase, for producing $H_2O_2$ by reaction with free cholesterol in the sample fluid, as described above. The glucose assay pad includes glucose oxidase, in addition to the common-pathway components. The triglyceride pad includes, in addition to the common-pathway components, lipase, L-glycerol kinase, and L-glycerol-3-phosphate oxidase, for generating $H_2O_2$ from triglyceride, via the intermediate L-glycerol-3-phosphate. The serum sample drawn into the TG pad is not exposed to precipitating or binding reagents, and thus contains all of the serum lipoproteins, so the TG signal represents total serum triglycerides.

Reference standard pads may also be employed; see, for example, the system described in co-owned U.S. Pat. No. 5,114,350, which is incorporated herein by reference.

As noted above, one advantage of the current device and method is that the sample distribution matrix does not contain non-HDL precipitating or binding reagents; such reagents are present only in reagent pad 74. Therefore, the possibility of interference by these reagents, in assays of analytes such as total serum cholesterol and total triglycerides, is eliminated.

EXAMPLES

The following examples illustrate but are in no way intended to limit the invention.

Example 1

Preparation of Reagent Membrane with Immobilized Binding Reagent

An aqueous solution containing 5-20 mg/ml dextran sulfate (500,000 MW) and (optionally) 12.5 mM $Mg(OAc)_2$ is dispensed onto a cationic membrane as described above, e.g. a nylon membrane having surface quaternary ammonium groups, having a thickness of about 125 $\mu$m. The reagent solution is dispensed at a rate of about 16 $\mu$l/inch, and the membrane is then dried for 20 minutes at 50° C. in a continuous roll process. Lengths of e.g. 100 feet can be prepared in this manner and cut to fit the assay devices.

Example 2

Preparation of HDL Test Membrane

To prepare an HDL reaction membrane, a polysulfone membrane is impregnated with the following aqueous formulation: cholesterol oxidase 36.5 Units/ml, cholesterol esterase 215 Units/ml, peroxidase 200 Units/ml, 4-aminoantipyrine 1.88 mg/ml, and TOOS (3-[ethyl(3-methylphenyl)amino]-2-hydroxy propanesulfonic acid) 12.05 mg/ml. The reagent is dispensed at a rate of 16.6 $\mu$l/inch, and the membrane is dried for 20 minutes at 50° C. in a continuous roll process. Lengths of e.g. 100 feet can be prepared in this manner and cut to fit the assay devices.

To prepare a laminated reagent/assay pad such as shown in FIG. 1, the two membranes, impregnated with reagent as above, are attached separately (sequentially) to the reaction bar by ultrasonic welding, or they may be attached simultaneously with a single ultrasonic weld step. The membranes may also be laminated together before application of reagents, and the respective reagents are then applied, first to one side of the laminate and then to the other.

Example 3

Representative Assay Procedure

A typical assay is carried out in an LDX® analyzer, using reagent pads and HDL test pads prepared essentially as described in Examples 1-2. For an assay device configuration as shown in FIG. 1, sample (35 $\mu$l of serum or whole blood) is applied to the sample well and allowed to distribute through the sample distribution matrix for 2 minutes. The reaction bar is then contacted with the matrix for 3 seconds, a time sufficient to transfer enough serum to fill the reagent pad and test pad (combined capacity about 1.5 $\mu$l), after which the bar is returned to its original position. Reflectance readings are taken from the upper surface of the HDL test pad every 3 seconds for 150 seconds, to monitor the progress of the HDL assay reaction. The minimum reflectance value attained is then converted to mg/dL of HDL cholesterol according to a previously established calibration curve.

It is claimed:

1. An assay device for performing a non-HDL assay in conjunction with measuring serum cholesterol associated with high-density lipoproteins (HDL) in a blood fluid sample also containing low density lipoproteins (LDL) or very low density lipoproteins (VLDL), the device comprising:
    (a) a plurality of porous elements through which said blood fluid sample can flow in sequence by capillary action and/or gravity, said plurality comprising:
        (i) a sample distribution matrix;
        (ii) an HDL test pad, downstream of said matrix, in which HDL concentration can be assayed;
        (iii) upstream of said HDL test pad, a reagent element containing an immobilized reagent, not soluble in the fluid sample, which is effective to selectively bind and remove non-HDL lipoproteins from the fluid sample; and
        (iv) a non-HDL test pad, downstream of said sample distribution matrix, in which a non-HDL assay may be performed, wherein a sample flow path to the non-HDL test pad does not contain said reagent element; and
    (b) mounting means effective to adjust the device between
        (a) a sample-distribution position, wherein the HDL test pad and the reagent element are not in fluid communication with the sample distribution matrix and are not in fluid communication with any element that removes cellular components, and further wherein the non-HDL test pad is not in fluid communication with the sample distribution matrix; and (b) a test position, wherein said HDL test pad, reagent element, and distribution matrix are in fluid communication with each other; while said non-HDL test pad is not in fluid communication with the reagent element.

2. The device of claim 1, wherein the reagent element is a porous reagent pad located downstream of the distribution matrix.

3. The device of claim 2, wherein the reagent pad is attached to the HDL test pad.

4. The device of claim 1, further comprising a reaction bar to which said HDL test pad is attached.

5. The device of claim 4, wherein said mounting means is effective to adjust the relative positions of the reaction bar between said sample-distribution position and said test position.

6. The device of claim 1, wherein said mounting means is further effective to
    (c) transfer the device from said test position to a position in which said HDL test pad is not in fluid communication with said sample distribution matrix.

7. The device of claim 1, wherein said HDL test pad comprises a biosensor.

8. The device of claim 7, wherein said biosensor is effective to electrochemically measure production of oxygen or hydrogen peroxide which is dependent on HDL-associated cholesterol concentration within said HDL test pad.

9. The device of claim 1, wherein said reagent element comprises a porous polymeric membrane.

10. The device of claim 9, wherein said polymeric membrane contains cationic surface groups.

11. The device of claim 1, wherein said reagent element comprises multiple stacked membranes, at least one of which contains an immobilized reagent effective to bind non-HDL lipoproteins.

12. The device of claim 1, wherein each of said HDL test pad and said reagent element is a porous polymeric membrane.

13. The device of claim 3, wherein the HDL test pad and reagent pad are laminated together.

14. An assay device for performing a non-HDL assay in conjunction with measuring serum cholesterol associated with high-density lipoproteins (HDL) in a blood fluid sample also containing low density lipoproteins (LDL) or very low density lipoproteins (VLDL), the device comprising:
    (a) a sample distribution matrix for distributing the blood fluid sample;
    (b) a reagent pad containing an immobilized reagent effective to selectively bind and remove non-HDL lipoproteins from the fluid sample;
    (c) an HDL test pad in which HDL concentration can be assayed, downstream of said reagent pad; and
    (d) a non-HDL test pad in which a non-HDL assay may be performed, wherein a sample flow path to the non-HDL test pad does not contain said reagent pad;
    wherein the HDL test pad and the reagent pad can be positioned so that they are not in fluid communication with the sample distribution matrix and are not in fluid communication with any element that removes cellular components, and further wherein the non-HDL test pad is not in fluid communication with the sample distribution matrix; and
    wherein said HDL test pad, reagent pad, and distribution matrix are brought into fluid communication with each other; while said non-HDL test pad is not in fluid communication with the reagent pad.

15. The device of claim 14, wherein said immobilized reagent comprises a sulfonated polysaccharide, and said reagent pad comprises a porous polymeric membrane having cationic surface groups.

16. The device of claim 1, wherein the HDL test pad includes a cholesterol-assaying enzyme reagent.

17. The device of claim 16, wherein the cholesterol-assaying enzyme reagent comprises cholesterol esterase and cholesterol oxidase.

18. The device of claim 1, wherein the immobilized reagent is dextran sulfate immobilized by electrostatic forces to the reagent element having positively charged surface groups.

19. An assay device for performing a non-HDL assay in conjunction with measuring serum cholesterol associated with high-density lipoproteins (HDL) in a blood fluid sample also containing low density lipoproteins (LDL) or very low density lipoproteins (VLDL), the device comprising:

(a) a plurality of porous elements through which said blood fluid sample can flow in sequence by capillary action and/or gravity, said plurality comprising:
   (i) a sample distribution matrix;
   (ii) an HDL test pad, downstream of said matrix, in which HDL concentration can be assayed;
   (iii) upstream of said HDL test pad, a reagent pad containing an immobilized reagent, wherein said immobilized reagent which is not soluble in the fluid sample, selectively binds and removes non-HDL lipoproteins from the fluid sample, and remains entrapped within said reagent pad; and
   (iv) a non-HDL test pad, downstream of said sample distribution matrix, in which a non-HDL assay may be performed, wherein a sample flow path to the non-HDL test pad does not contain said reagent element; and (b) mounting means effective to adjust the device between (a) a sample-distribution position, wherein the HDL test pad and the reagent element are not in fluid communication with the sample distribution matrix and are not in fluid communication with any element that removes cellular components, and further wherein the non-HDL test pad is not in fluid communication with the sample distribution matrix; and (b) a test position, wherein said HDL test pad, reagent element, and distribution matrix are in fluid communication with each other; while said non-HDL test pad is not in fluid communication with the reagent element.

20. The device of claim 19, wherein said non-HDL assay is a total cholesterol assay.

21. The device of claim 19, wherein said non-HDL assay is a triglyceride assay.

* * * * *